US006177088B1

(12) United States Patent
Guo et al.

(10) Patent No.: US 6,177,088 B1
(45) Date of Patent: Jan. 23, 2001

(54) SURFACE-FUNCTIONALIZED, PROBE-CONTAINING NANOSPHERES

(75) Inventors: Congyuan Guo, Columbia; Rhys N. Thomas, Fayette, both of MO (US)

(73) Assignee: Fayette Environmental Services, Inc., Fayette, MO (US)

( * ) Notice: Under 35 U.S.C. 154(b), the term of this patent shall be extended for 0 days.

(21) Appl. No.: 09/226,233

(22) Filed: Jan. 7, 1999

(51) Int. Cl.$^7$ .............................. A61K 9/14; A61K 47/02; A61K 51/12
(52) U.S. Cl. ......................... 424/400; 428/407; 424/1.53
(58) Field of Search ............................................. 424/400

(56) References Cited

U.S. PATENT DOCUMENTS

| | | |
|---|---|---|
| 4,501,726 | 2/1985 | Schröder et al. . |
| 5,718,905 | 2/1998 | Skiba et al. . |

FOREIGN PATENT DOCUMENTS

| | | |
|---|---|---|
| 99/46204 | * 9/1999 | (WO) . |
| WO 99/46204 | * 9/1999 | (WO) . |

OTHER PUBLICATIONS

Nanophase Materials G.C. Hadjipanayis pp. 8, 9, Jun. 7, 1993.*

Abstract of Papers A. Mayer et al 216$^{th}$ ACS Meeting Boston, Aug. 1998.*

Chem. Comm. Jul. 21, 1998 pp. 1439–1440.*

J. Am. Chem. Soc. Nov. 19, 1999 121 10642–10643.*

R. R. Shankar, "Study Of Probe–Containing Surface–Functionalized Nanospheres", Ph.D. *Dissertation*, University of Missouri, Columbia, 1991, pp. 70–128.

C. Guo, "The Synthesis of Surface–Functionalized Probe–Containing Nano-spheres for Bioanalysis," *Dissertation*, University of Missouri, Columbia, 1991, pp. 69–102.

Guo, et al. "Synthesis of Surface–Functionalized, Probe–Containing Polymerized Vesicles Derived from Ammonium Bromide Surfactants," *Langmuir*, vol. 8, pp. 815–823 (1992).

Guo, et al. "Functionalized, Probe–Containing, Latex Nanospheres," *Anal. Biochem.*, vol. 207, pp. 241–248 (1992).

Molday, et al. "New Immunolatex Spheres: Visual Markers of Antigens on Lymphocytes for Scanning Electron Microscopy," *J. Cell Biol.*, vol. 64, pp. 75–88 (1975).

Gref, et al. "Biodegradable Long–Circulating Polymeric Nanospheres," *Science*, vol. 263, pp. 1600–1603 (1994).

Serizawa, et al. "Unusual Size Formation of Polymeric Nanospheres Synthesized by Free Radical Polymerization in Ethanol–Water Mixed Solvents," *Langmuir*, vol. 14, pp. 1278–1280.

Thurmond, II, et al. "Shell Cross–Linked Knedels: A Synthetic Study of the Factors Affecting the Dimensions and Properties of Amphiphilic Core–Shell Nanospheres," *J. Am. Chem. Soc.*, vol. 119, pp. 6656–6665 (1997).

Huang, et al. "Hydrogel–Coated Glassy Nanospheres: A Novel Method for the Synthesis of Shell Cross–Linked Knedels," *J. Am. Chem. Soc.*, vol. 119, pp. 11653–11659 (1997).

* cited by examiner

Primary Examiner—Peter F. Kulkosky
(74) Attorney, Agent, or Firm—Joan L. Simunic; Stites & Harbison

(57) ABSTRACT

The present invention relates to a series of nanospheres, having diameters of less than about 50 nm, and having probe ion cores surrounded by layers of surfactant and by a polymer shell. The surface of the shell is functionalized with acid compounds, at least one of which includes a spacer between the nanosphere surface and the acid functionality. In some alternative embodiments, the surface is also functionalized with long-chain ester and alcohol groups. The probe ion core improves the sensitivity and reproducibility of immunoassay procedures. The acid compounds on the surface minimize self-agglomeration of the nanospheres and improve the coupling of the nanosphere with antibodies. The ester and alcohol groups enhance the aqueous suspension characteristics and the shelf life of the nanospheres.

29 Claims, No Drawings

SURFACE-FUNCTIONALIZED, PROBE-CONTAINING NANOSPHERES

GOVERNMENT INTEREST

The invention was made with Government support under contract number 68D60030 awarded by the U.S. Environmental Protection Agency Small Business Innovation Research Program. The Government has certain rights in this invention.

BACKGROUND

This invention relates to nanospheres with acid-functionalized polymeric outer shells and surfactant-surrounded probe ion cores, and to a method for making the nanospheres.

Immunoassay, used for detecting and quantitating organic compounds, or analytes, is a well-known analytical technique. In an immunoassay procedure, an excess quantity of an antibody known to complement a particular analyte, is exposed to a test sample containing the analyte. The analyte binds to the antibody, forming an antibody-analyte conjugate. The conjugate is isolated and measured spectroscopically or electrochemically, and the results are extrapolated to determine the level of analyte in the material tested. In a conventional immunoassay procedure, the antibody or the analyte—the host—is labeled with a dye or with enzymes, which react with other reagents to produce colored products. The dye or colored product make it easier to detect and measure the amount of conjugate formed.

Although immunoassay is a highly sensitive means for detecting organic compounds in complex mixtures, such as those found in medical, biochemical, and environmental applications, the immunoassay technique has some serious shortcomings. For example, the sensitivity is often less than desired, meaning analytes present at very low concentrations may not be detected; and the coefficient of variability between replicates is relatively high, so it can be difficult to accurately determine the concentration of the analyte present in a particular sample. The dye-labeled antibodies or analytes, in particular, suffer from low sensitivity, because only a limited number of dye molecules can be coordinated with a host without inactivating the host. With enzyme-labeled antibodies or analytes, the sensitivity is increased because a single enzyme associated with a host can essentially produce an unlimited number of colored product molecules, but the reproducibility suffers because the rate of reaction between the enzyme and the other reagents, to produce the colored product molecules, is highly dependent on reaction time and temperature.

The immunoassay technique is also not very effective for analyzing solid samples, such as soils, because the analytes typically must be extracted from the sample before the immunoassay is performed, a time-consuming and waste-generating procedure. The extraction procedure also causes the analyte to be diluted, making detection more difficult. Further, the analyte must be known a priori, limiting the procedure to one, pre-selected contaminant.

The sensitivity is increased, and the reproducibility is improved, when the signal generated from the antibody-analyte conjugate is amplified, such as with the fluorescent rare earth ions, terbium(III) and europium(III), referred to as probe ions. Single probe ions are linked to antibodies using molecules of bifunctional chelating reagents, such as 1-(p-benzenediazonium)-EDTA or 4,7-bis(chlorosulfophenyl)-1,10-phenanthroline-2,9-dicarboxylic acid. However, the number of molecules of chelating reagents that can coordinate to a particular antibody is limited, with the average ratio of chelating reagent molecules linked to antibodies being less than 10. At this ratio, signal amplification from the probe ions is not strong enough to significantly alter the sensitivity of the procedure.

The patentee has previously shown that it is possible to concentrate terbium(III) ions by encapsulating them within a polystyrene, or latex, shell to form a bead having a diameter as small as 50 nm, and then to couple antibodies to the bead. Beads having diameters in the nanometer-scale range are generically referred to as nanospheres, and nanospheres with diameters of about 50 nm can contain up to about 40,000 terbium(III) ions. This high concentration of probe ions can significantly improve the sensitivity and reproducibility for immunoassay. However, coupling antibodies to the probe-containing nanospheres can be problematic. For example, bead surfaces have been functionalized with methacrylic acid groups only, and with amine plus methacrylic acid groups, in an attempt to facilitate the nanosphere-antibody coupling reaction. (See "Functionalized, Probe-Containing, Latex Nanospheres", *Anialytical Biochemistry*, 207, 241 (1992), and "The Synthesis of Surface-Functionalized Probe-Containing Nanospheres for Bioanalysis", C.-Y. Guo Dissertation, University of Missouri-Columbia (April, 1991), both articles incorporated herein by reference.) Antibodies coupled with the methacrylic acid functionalized nanospheres very poorly: either the antibodies did not couple with the nanospheres at all, or so many antibodies became attached to a single nanosphere that the antibodies became stressed and essentially inactive. Nanospheres functionalized with amine and methacrylic acid groups tended to conjugate more with each other than with antibodies, resulting in very low yields of nanosphere-antibody conjugates.

In addition, a nanosphere having a diameter of about 50 nm is relatively large as compared to an antibody, so when the nanosphere is conjugated to the antibody, the mobility of the conjugate is reduced as compared to an unconjugated antibody, increasing the time necessary for the nanosphere-antibody conjugate to contact and react with an analyte. However, producing nanospheres smaller than about 50 nm is extremely difficult because so many factors affect the nanosphere size, including how the probe ions are prepared prior to encapsulation within the polymer shell, and how the polymer shell is formed.

SUMMARY OF THE INVENTION

The present invention relates to a series of nanospheres, having diameters of less than about 50 nm, and having probe ion cores surrounded by layers of surfactant and by a polymer shell. The surface of the shell is functionalized with acid compounds, at least one of which includes a spacer between the nanosphere surface and the acid functionality.

The surface-functionalized, probe-containing nanospheres can be coupled to antibodies, analytes, or other compounds of immunological significance and can be used, for example, in immunoassay analyses. The probe ion core improves the sensitivity and reproducibility of the immunoassay procedure. The acid compounds on the surface minimize self-agglomeration of the nanospheres, improving the degree of coupling with antibodies or other proteins. In addition, the spacer separates the acid functionality from the nanosphere surface, significantly improving the degree of coupling between the nanospheres and antibodies, providing greater flexibility to the antibody coupled to the nanosphere, and reducing the steric stress on the antibody when the antibody is conjugated to a single nanosphere at several places.

In some alternative embodiments, the surfaces are also functionalized with long-chain ester and alcohol groups. The ester and alcohol groups enhance the aqueous suspension characteristics of the nanospheres, thereby reducing the rate of precipitation of the nanospheres. Nanospheres functionalized with acids, esters, and alcohols have a longer shelf life, and produce nanosphere-antibody conjugates in higher yields, than nanospheres functionalized with acids alone.

DETAILED DESCRIPTION OF THE INVENTION

Structure of the Nanosphere

The nanosphere of the present invention is a nanometer-scale bead having a surfactant-surrounded probe ion core and an acid-functionalized polymer shell. The beads are essentially spherical, and have relatively uniform size distribution, ranging in diameter from about 10 nm to about 50 nm. Preferably, the beads have a nominal diameter of about 30±10 nm.

The probe ion core can be any nanometer-scale complex that can be detected spectroscopically with or without an imaging agent, and can be formed from an ionic salt that can be crystallized as a nanometer-scale crystal, or precipitated as a nanometer-scale particle, in an organic solvent. The ionic salt can be any water soluble inorganic anion or cation having a labile counterion. Some example ionic salts include dysprosium(III) chloride, europium(III) chloride, gadolinium(III) chloride, iron(II) chloride, iron(III) chloride, niobium(V) chloride, osmium(III) chloride, ruthenium(III) chloride, samarium(III) chloride, tantalum (V) chloride, terbium (III) chloride, and combinations thereof, and the borates, the metaborates, the arsenates, the silicates, and combinations thereof. The probe ion core can be the precipitate of the ionic salt, or the crystalline reaction product obtained by reacting the ionic salt with a base. Ionic salts which can be precipitated to form probe ion cores include sodium meta-borate, sodium arsenate, sodium silicate, and combinations thereof Probe ion cores which are formed by the reaction of the ionic salt with a base include the product from the reaction of terbium(III) chloride hexahydrate and sodium bicarbonate, the product from the reaction of tantalum(V) chloride and sodium bicarbonate, the product from the reaction of ruthenium(III) chloride and sodium bicarbonate, and the product from the reaction of iron (II) chloride and iron (III) chloride with ammonium hydroxide, among others.

The crystalline probe ion core is surrounded by a first layer of anionic surfactant molecules, the surfactant being a linear or branched organic compound having an anionically charged head portion and a non-polar tail portion, with the distance between the head and the terminus of the tail defining the length of the surfactant. The surfactant molecules are oriented so the heads are next to the probe ion core, and the tails form a relatively compact outer sphere. A second layer of an anionic surfactant covers the first layer. The second layer surfactant also has an anionically charged head portion and a non-polar tail portion. The surfactant molecules of the second layer are oriented tail-to-tail with the first layer. The two surfactant layers, although relatively compact, should be sufficiently permeable to allow organic or organometallic complexes to traverse the layers and interact with the probe ion core to form spectroscopically detectable complexes. The first and second layer surfactants are selected such that the length of the first surfactant added to the length of second surfactant approximates the desired radius of the nanosphere. Example surfactants include sodium dodecyl sulfate, sodium dioctyl sulfosuccinate, or combinations thereof The surfactants of the first and second layers may be the same compound or may be different compounds.

The surfactant-surrounded probe is further surrounded by a semi-permeable polymer semi-permeable shell, generated in situ from monomers and, in some embodiments, cross-linkers. The precise position of the polymer shell relative to the first and second surfactant layers is not known, but it is speculated that the non-polar monomers and cross-linkers diffuse into the region between the two layers of non-polar tails, and create a web of polymer which holds the surfactant layers in their relative positions. The polymer shell must be sufficiently impermeable to ensure that the surfactant-surrounded probe cannot diffuse from the shell, but sufficiently permeable to allow organic or organometallic compounds to traverse the shell and interact with the probe ion core.

The monomers can be any polymerizable, organic molecules, such as styrene or methyl methacrylate, that will produce a polymer chain. The cross-linkers, which are added to increase the impermeability of the shell, can be any non-polar organic molecules that can interconnect two independent polymer chains, such as divinyl benzene or butadiene. The higher the degree of cross-linking, the greater the impermeability. If the monomer produces a shell having acceptable permeability characteristics, it is not necessary to include a cross-linker, and when cross-linkers are added, one or more cross-linking agents may be used simultaneously, in order to achieve the optimum spacing between the chains. For example, shells can be made from a styrene monomer cross-linked with divinyl benzene, butadiene, 2,3-dimethyl-1,3-butadiene, or combinations thereof. When shells are made from styrene monomer with divinyl benzene and 2,3-dimethyl-1,3-butadiene cross-linkers, the divinyl benzene and butadiene provide structure to the shell, and the methyl groups on the 2,3-dimethyl-1,3-butadiene serve to block the probes from exiting the shells prematurely.

The surface of the nanosphere is functionalized with a first organic acid, having a spacer. The spacer acid can be any organic compound that has an acid functional group, a terminal olefin, and a spacer of more than approximately 5 Å in length, such as a phenyl ring or a linear chain of at least 4 carbon atoms, between the acid functionality and the olefin. The spacer acid is attached to the polymer chains forming the shell by the terminal olefin, with the acid functional group extending away from the probe ion core. That is, the spacer acid becomes incorporated into the polymer chains of the shell. Examples of spacer acids which can be used include 4-vinyl benzoic acid, citronellic acid, and combinations thereof.

The surface can further be functionalized with a second organic acid. The second acid can be any organic compound that has both an acid functional group and a terminal olefin. The second acid is attached to the polymer chains forming the shell by the terminal olefin, with the acid functional group extending away from the probe ion core. An example of a second acid is methacrylic acid.

The spacer and second acids, which may further include substituents such as alkyl side chains, help retain the probe ion core within the shell, through steric and polar hindrance. The acids sterically hinder the movement of the probe ion core by filling void spaces that may otherwise exist in the polymer shell and surfactant layers, particularly when the acid includes alkyl substituents. Polar hindrance is created because the organic acids increase the non-polar space that must be traversed by the polar probe ion core.

The organic acids on the shell surface also aid in the conjugation of the nanosphere with an antibody because the negative charge of the acid functionality of the nanosphere associates electrostatically with a positively-charged amine functionality of the antibody. This association increases the probability of a coupling reaction occurring between the nanosphere and the antibody, even in a dilute solution. The spacer on the first organic acid significantly improves the probability of such coupling. It has been observed that nanospheres functionalized only with organic acids that did not include spacers conjugate with antibodies only about 15% as well as those nanospheres in which about 50% of the organic acids include spacers. The enhanced conjugation performance of the nanospheres with spacer acids may result because the spacer provides a means for the acid functionality to extend through the surfactant layers to reach the exterior surface of the nanosphere. The spacer acid also allows the bound antibody more flexibility of movement than if it were held closer to the surface.

Nanospheres having only organic acids on the surface will be referred to herein as Type A nanospheres. That is, a Type A nanosphere will have the probe ion core; the first surfactant layer surrounding the probe ion core; the second surfactant layer surrounding the first surfactant layer; the polymer shell encasing the probe ion core—the specific position of the polymer shell being unknown, but assumed to be between the first and second surfactant layers; the spacer acid attached to the polymer shell; and, optionally, the second organic acid attached to the polymer shell.

Type A Embodiment: A nanosphere has a probe ion core made by reacting terbium chloride hexahydrate with sodium bicarbonate; a first surfactant layer of sodium dioctyl sulfosuccinate; a second surfactant layer of sodium dodecyl sulfate; a shell made of polystyrene, with divinyl benzene and 2,3-dimethyl-1,3-butadiene cross-linkers; and a surface functionalized with a spacer acid, 4-vinyl benzoic acid, and a second organic acid, methacrylic acid. (Details for preparation of this embodiment are provided infra in Example 1.)

Type A nanospheres tend to have relatively poor suspension characteristics, and thus, tend to precipitate rapidly. Functionalizing the nanosphere surface with a combination of organic acids, esters and/or organic alcohols improves the suspension characteristics, and reduces the rate of precipitation. These multi-functional nanospheres, referred to herein as Type B nanospheres, have a longer shelf life and produce nanosphere-antibody conjugates in higher yields than the Type A nanospheres.

The Type B nanospheres are similar to the Type A nanospheres, except that the polymer shell surface is further functionalized with an ester, an organic alcohol, or a combination thereof The ester can be any organic compound that has both an ester functional group and a terminal olefin, and can further include other substituents. One or more esters can be used simultaneously. The organic alcohol can be any organic compound that has both an alcohol functional group and a terminal olefin, and can further include other substituents. One or more organic alcohols can be used simultaneously. The terminal olefins of the ester and the alcohol attach the compounds to the polymer chains forming the shell. Preferably, the Type B nanosphere includes at least one spacer acid, at least one ester, and at least one organic alcohol. Compounds can be selected to deliver more than one functional group. For example, the surface can be functionalized with 4-vinyl benzoic acid (providing the spacer acid) and with 2-hydroxyethyl methacrylate (providing the ester and organic alcohol).

Type B Embodiment: A nanosphere has a probe ion core, a first surfactant layer, a second surfactant layer, and a shell made of polystyrene, a s described in the Type A Embodiment. The shell surface is functionalized with spacer acids, 4-vinyl benzoic acid and citronellic acid; a second organic acid, methacrylic acid; and an ester and organic alcohol source, 2-hydroxyethyl methacrylate. (Details for preparation of this embodiment are provided infra in Example 11.)

Preparation of the Nanospheres

The Type A and Type B nanospheres are prepared in a multi-step process that involves preparing reverse micelles with the probe ion core at the center and the first anionic surfactant surrounding the probe ion, adding the second anionic surfactant to the reverse micelles to create double micelles with the probe ion core at the center, incorporating a polymer shell with the double micelles, functionalizing the surface of the shell, and isolating the functionalized nanospheres.

The reverse micelles are prepared by allowing the first anionic surfactant to interact with the ionic salt in the non-polar, organic solvent, and then adding the base, if necessary. The organic solvent can be any non-polar compound, such as hexane, cyclohexane, heptane, pentane, petroleum ether, or combinations thereof. The first surfactant, ionic salt, and organic solvent are essentially the same as described for the Type A nanospheres. Organic solvents with densities less than about 1.0 and with boiling points below about 100° C. are easiest to handle in subsequent steps.

A surfactant/ionic salt micelle is formed by adding the first surfactant to the organic solvent at a concentration of from about five to about seven times its critical micelle concentration, i.e. the concentration above which micelle formation becomes appreciable. The surfactant must be thoroughly dispersed in the solvent, and can be sonicated, if necessary, without adversely affecting the surfactant. The ionic salt is then added to the organic solvent, either undiluted or dissolved in water, so that the salt is dispersed in the solvent as nanometer-scale particles or droplets. If the dissolved salt is added to the organic solvent, it may be necessary to sonicate the solvent to cause the salt water to disperse in the solvent as nanometer-scale droplets. The solvent temperature should be maintained below about 20° C., while the salt water is dispersed.

The surfactant forms an essentially spherical layer of film, or a surfactant sphere, around the nanometer-scale particles or droplets, with the head of the surfactant directed inward. The resultant micelles should be smaller than the wavelengths of visible light, and not visible with the naked eye. If the surfactant/ionic salt mixture is turbid, the mixture can be subjected to sonication to further disperse the reagents, without negatively affecting the surfactant ionic salt interaction, provided the solvent temperature is maintained at below about 20° C.

The base, if used, is then added to the micelle solution, carefully controlling the rate of addition to prevent precipitation of the micelles. The base solidifies the ionic salt within the surfactant sphere, producing a crystalline material, the exact formulation of which is unknown, but is believed to be either a metal oxide or a metal hydroxide complex. The first surfactant encapsulates the nanometer-scale particles or droplets of ionic salt during the crystallization process, thereby limiting crystal growth to the material within the surfactant sphere, and forming nanometer-scale crystals, oe nanocrystals. The nanocrystals are the probe ion core. The crystalline probe ion core surrounded by the first surfactant, with the tails of the surfactant being away from the probe ion core, is the reverse micelle.

The double micelle is formed by allowing the reverse micelle to react with the second anionic surfactant dispersed in aqueous solution. The second anionic surfactant is essentially the same as described for the Type A nanospheres, and when in aqueous solution, the second surfactant forms a normal micelle (micelle with the surfactant heads facing outward, toward the reaction media). To form the double micelle, an aqueous solution of the second surfactant, at a concentration of from about five times to about seven times its critical micelle concentration, is slowly added to the reverse micelle organic solvent. At the aqueous/organic solvent interface, the reverse micelle migrates into the center of the normal micelle, so that the tails of the first and second surfactants are in contact with each other, and the probe ion core is encased within the first and second surfactant layers. Because the double micelle is oriented such that the charged head is on the outer surface, the double micelle preferentially migrates into the aqueous solution. The double micelle yield can be improved by slowly evaporating most of the organic solvent layer to force the reverse micelles toward the solvent interface. Retaining a thin layer of organic solvent helps prevent the double micelles from adhering to the sides of the reaction vessel. After the double micelle has been formed, the aqueous solution is transferred to a reaction vessel maintained under an inert atmosphere.

The double micelle is then encapsulated in a polymer shell, and the surface is functionalized, by adding the organic monomer, the cross-linking agent (if used), the surface functionalizing compounds, and an initiator, to the aqueous solution. The monomer, the cross-linking agent, and the surface-active acid, are essentially the same as described for the Type A nanospheres. The initiator can be any reagent that undergoes thermolysis to begin the polymerization reaction, such as persulfate or organic peroxides, or any suitable radical initiator, such as ultraviolet light. The reagents, excluding the initiator, should be mixed until a homogeneous micelle/monomer solution is formed. The order of addition of the materials can be varied, provided a homogenous solution is maintained. The initiator is dispersed throughout the micelle/monomer solution at ambient temperature with mixing, after all other reagents have been added. The solution is then heated to the activation temperature of the initiator, and the reaction is allowed to proceed to completion, maintaining heating and stirring. The solution is then slowly cooled to ambient temperature.

The nanospheres can be cleaned and collected by filtering, dialysis, ion exchange, or centrifugation. Filtration is generally less damaging to the nanospheres, i.e. the nanosphere recovery is highest with filtration, and filtration is the preferred collection method for the Type B nanospheres because these nanospheres do not easily precipitate, even with centrifugation. Centrifugation can be used to collect the Type A nanospheres. Excess small molecules can be removed by dialysis. Excess ions and surfactants can be removed by ion exchange.

At this stage, the nanospheres can be stored in aqueous buffered solution, lyophilized, or air dried at room temperature. Dried nanospheres stored in a sealed container are not particularly susceptible to oxidation, and they are not particularly hygroscopic. However, the nanospheres solutions and dried nanospheres are temperature sensitive, and can decompose, fuse, or rupture at temperatures greater than about 50° C. The dried nanospheres may be resuspended in an aqueous buffer by stirring or shaking. Nanosphere solutions and dried nanospheres have been shown to have a shelf life in excess of one year.

The following examples illustrate and explain the present invention, but are not to be taken as limiting the present invention in any regard.

EXAMPLE 1

In a preferred embodiment, a Type A nanosphere is prepared using materials obtained from Aldrich Chemical Company, 1001 West Saint Paul Avenue, Milwaukee, Wis., 53233. Where indicated, solutions are sonicated at 50% full power using an ultrasonic processor, manufactured by Ultrasonics, 1938 New Highway, Farmingdale, N.Y. 11735, and sold under model designation Heat Systems W-225. The ultrasonic processor is fitted with a water jacket receptor suitable for holding a 100 mL beaker. The nanospheres are prepared as follows:

In a first 100 mL beaker, the first surfactant, 110 mg sodium dioctyl sulfosuccinate (98%, catalog number 32,358-6), is added to 10±1 mL heptane (99%, spectroscopic grade, cat. no. 15,487-3). The solution can be sonicated to assist in dissolution. With the beaker still in the sonicator bath, and the temperature held below about 20° C., the ionic salt, 100 $\mu$L of a 1.25 M terbium chloride hexahydrate stock solution (467 mg $TbCl_3 \cdot 6H_2O$ dissolved in 1 mL $H_2O$; to deliver 46.7 mg $TbCl_3 \cdot 6H_2O$; 99.9%, cat. no. 21,290-3) is added and dispersed. If the $TbCl_3 \cdot 6H_2O$ solution does not disperse, it can be sonicated for about 2 minutes, holding the temperature below about 20° C. The solution should appear clear. Without sonication, the base, 50 mg sodium bicarbonate (99.7%, cat. no. 23,652-7) is added, taking care to not cause precipitation. This is the reverse micelle solution.

In a second 100 mL beaker, the second surfactant, 562 mg sodium dodecyl sulfate ("SDS", 98%, cat. no. 86,201-0), is added to 40±1 mL of distilled water. The solution is sonicated for 3 minutes to ensure complete dispersion of the SDS—the solution should appear clear to the naked eye. The aqueous solution of SDS is poured into the first beaker containing the reverse micelle solution. The combined solutions have a milky appearance. The mixture is sonicated for 10 minutes. After sonication is complete, the heptane layer is nearly clear while the aqueous layer has a milky appearance. The first beaker is removed from the sonicator and the heptane layer is allowed to evaporate at room temperature until all but a thin layer of heptane is evaporated. The resulting aqueous solution contains the double micelles.

The aqueous solution is then transferred to a 250 mL three-necked, round-bottomed, glass reaction flask fitted with a gas inlet, a stopper, and a Friedrich condenser, having an output port that is vented by a rubber septum pierced with a needle. Before the aqueous solution is transferred to the flask, essentially all oxygen is purged from the flask and condenser, and is replaced by argon. Argon flow is maintained throughout the encapsulation and functionalization steps. The reaction flask is immersed in a temperature-monitored, silicon oil bath, and the aqueous solution is agitated so as to create a vortex. Before the aqueous solution is heated, the monomer, 3000 $\mu$L styrene (99%, cat. no. S497-2), the cross-linkers, 100 $\mu$L divinyl benzene (80%, cat. no. 41,456-5) and 320 $\mu$L 2,3-dimethyl-1,3-butadiene (98%, cat. no. 14,549-1), the spacer acid, 391 mg 4-vinyl benzoic acid (97%, cat. no. 25,473-8), and the second organic acid, 220 $\mu$L methacrylic acid (99%, cat. no. 39,537-4), are added to the flask, and mixed until the solution is homogeneous. The initiator, 72 mg potassium persulfate (99+%, cat. no. 21,622-4) dissolved in about 3 mL distilled water, is then added to the flask. The reaction is heated to about 70° C., and maintained between 65° C. and 75° C., for about 20 hours. The solution contains the Type A nanospheres.

The Type A nanospheres are collected by centrifuging the solution at 3200 rpm for 10 minutes at 20° C., then resuspending the solids in morpholino ethane sulfonic acid and stirring for more than about 10 hours, and then collecting the nanospheres on membrane filters, having pores of from about 100 nm to about 450 nm. Approximately 3 g of nanospheres, ranging in size from about 20 nm to about 45 nm, are obtained.

EXAMPLE 2

The nanospheres are prepared as in Example 1, except that the ionic salt is 100 μL of a 0.5 M ruthenium(III) chloride hydrate stock solution (cat. no. 20,622-9). The reaction is maintained between 65° C. and 75° C., for about 19.5 hours. Approximately 3 g of nanospheres, ranging in size from about 15 nm to about 40 nm, are obtained.

EXAMPLE 3

The nanospheres are prepared as in Example 1, except that the ionic salt is 100 μL of a 1.0 M europium(III) chloride hexahydrate stock solution (cat. no. 20,325-4). The reaction is maintained between 65° C. and 75° C., for about 18 hours. Approximately 3 g of nanospheres, ranging in size from about 12 nm to about 32 nm, are obtained.

EXAMPLE 4

The nanospheres are prepared as in Example 1, except that the ionic salt is 100 μL of a 1.0 M samarium(III) chloride hydrate stock solution (cat. no. 24,880-0); the spacer acid is 0.116 g 4-vinyl benzoic acid; and the second organic acid is 380 μL methacrylic acid. The reaction is maintained at about 70° C., for about 17.5 hours. Approximately 3 g of nanospheres, ranging in size from about 20 nm to about 40 nm, are obtained.

EXAMPLE 5

The nanospheres are prepared as in Example 4, except that the ionic salt is 100 μL of a 1.0 M dysprosium(III) chloride hexahydrate stock solution (99.9%, cat. no. 28,927-2). The reaction is maintained between 65° C. and 75° C., for about 16 hours. Approximately 3 g of nanospheres, ranging in size from about 15 nm to about 40 nm, are obtained.

EXAMPLE 6

The nanospheres are prepared as in Example 4, except that the ionic salt is 200 μL of an approximately 0.0056 M tantalum(V) chloride hydrate stock solution (cat. no. 40,047-5). The reaction is maintained at about 70° C., for about 22.5 hours. Approximately 3 g of nanospheres, ranging in size from about 20 nm to about 45 nm, are obtained.

EXAMPLE 7

The nanospheres are prepared as in Example 1, except that the ionic salt is 100 μL of a 0.667 M sodium metaborate hydrate stock solution (cat. no. 22,870-2); the spacer acid is 0.100 g 4-vinyl benzoic acid; and the second organic acid is 380 μL methacrylic acid. The reaction is maintained at about 70° C., for about 20 hours. Approximately 3 g of nanospheres, ranging in size from about 15 nm to about 40 nm, are obtained.

EXAMPLE 8

The nanospheres are prepared as in Example 1, except that the ionic salt is 100 μL of Fe(II)/Fe(III) solution (Fe(II)/Fe(III) solution is prepared by dissolving 1.99 g $FeCl_2 \cdot 4H_2O$ in 3 mL water, and 1.49 g $FeCl_3 \cdot 6H_2O$ in 3 ml water, then mixing the Fe(II) and Fe(III) solutions), the base is 70 μL of 25% ammonium hydroxide solution, and the second organic acid is 440 μL methacrylic acid. Approximately 3 g of nanospheres, ranging in size from about 10 nm to about 35 nm, are obtained.

EXAMPLE 9

The nanospheres are prepared as in Example 4, except that the ionic salt is 100 μL of a 1.0 M osmium(III) chloride stock solution (99.9%, cat. no. 39,859-4). The reaction is maintained between 65° C. and 75° C., for about 16 hours. Approximately 3 g of nanospheres, ranging in size from about 20 nm to about 45 nm, are obtained.

EXAMPLE 10

The nanospheres are prepared as in Example 4, except that the ionic salt is 100 μL of a 1.0 M gadolinium(III) chloride hexahydrate stock solution (cat. no. 27,852-1). The reaction is maintained between 65° C. and 75° C., for about 18 hours. Approximately 3 g of nanospheres, ranging in size from about 15 nm to about 45 nm, are obtained.

EXAMPLE 11

A Type B nanosphere is prepared similar to the Type A nanosphere of Example 1, except that the first surfactant is 200 mg sodium dioctyl sulfosuccinate added to 10±1 mL heptane; the ionic salt is 200 μL of a 1.25 M terbium chloride hexahydrate solution; the cross-linkers are 200 μL divinyl benzene and 320 μL 2,3-dimethyl-1,3-butadiene; the spacer acids are 391 mg 4-vinyl benzoic acid and 300 μL citronellic acid; the second organic acid is 100 μL methacrylic acid; the ester and organic alcohol source is 300 μL 2-hydroxyethyl methacrylate. The ester and organic alcohol are added with the organic acids, before the initiator is added. The reaction is maintained between 65° C. and 75° C., for about 20 hours. Approximately 3 g of nanospheres, ranging in size from about 20 nm to about 45 nm, are obtained.

EXAMPLE 12

A Type B nanosphere is prepared as in Example 11, except that the first surfactant is 200 mg sodium dioctyl sulfosuccinate added to 15±1 mL heptane; the monomer is 3000 μL methyl methacrylate (cat. no. M5,590-9); the cross-linker is 350 μL 2,3-dimethyl-1,3-butadiene; and the spacer acid is 300 μL citronellic acid. The reaction is maintained between 65° C. and 75° C., for about 20 hours. Approximately 3 g of nanospheres, ranging in size from about 20 nm to about 45 nm, are obtained.

EXAMPLE 13

The Type A nanospheres of Example 1 are coupled with goat anti-rabbit antibodies by the following procedure: 80 μL of 2.7 mg/mL goat anti-rabbit IgG in phosphate buffer solution is added to 800 μL of 0.023% (w/w) nanospheres in morpholino ethane sulfonic acid solution, and mixed by vortex. To the nanosphere solution is added 30 μL of 10 mg/mL 1-ethyl-3-(3-dimethylaminopropyl) solution, and mixed by vortex. The solution then is shaken gently for about 2 hour at ambient temperature.

It will be obvious to those skilled in the art that modifications may be made to the embodiments and examples described above without departing from the scope of the present invention.

What is claimed is:

1. A nanometer-scale bead, having an essentially spherical shape and a diameter of from about 10 nm to about 50 nm, said nanosphere comprising:

a nanometer-scale probe ion core, formed from an ionic salt consisting of any water soluble inorganic anion or cation having a labile counterion;

a molecular layer of a first anionic surfactant, surrounding said probe ion core;

a molecular layer of a second anionic surfactant, surrounding said probe ion core and said first aninic surfactant layer such that the surfactant molecules of said second surfactant are oriented tail-to-tail with the molecules of said first surfactant;

a semi-permeable polymer shell, being formed of polymer chains formed from a polymerizable organic monomer by the addition of an initiator, and encasing said probe ion core within said shell; and a first organic acid having an acid functionality, a terminal olefin and a spacer of at least 5 Å between the acid functionality and the olefin, said first organic acid being incorporated into the polymer chains of said polymer shell, the nanosphere being formed by the steps of:
(a) dispersing said first anionic surfactant in a non-polar organic solvent;
(b) dispersing said second anionic surfactant in an aqueous solution;
(c) adding a concentrated aqueous solution of said ionic salt to said surfactant-containing organic solvent, allowing said salt to be dispersed into said first surfactant to form a reverse micelle;
(d) adding said surfactant-containing organic solvent to said surfactant-containing aqueous solution, and allowing the reverse micelle to be dispersed into said second surfactant to form a double micelle;
(e) evaporating said organic solvent away from said aqueous solution containing said double micelles;
(f) adding to said double-micelle-containing aqueous solution said polymerizable monomer and said first organic acid having an acid functionality, a terminal olefin, and a spacer of at least 5 Å;
(g) then adding to said aqueous solution said initiator, and activating said initiator, while mixing said aqueous solution, and allowing a polymerization reaction to proceed until the reaction is essentially complete and said double micelles are encapsulated in polymer shells to form nanospheres wherein each nanosphere has a diameter of from about 10 nanometers to about 50 nanometers; and
(h) removing said aqueous solution from the nanospheres.

2. The nanosphere as recited in claim 1, wherein said probe ion core is produced by adding a base to said organic solvent after formation of the reverse micelles from said first surfactant and said ionic salt.

3. The nanosphere as recited in claim 1, wherein said ionic salt is selected from the group consisting of dysprosium(III) chloride, europium(III) chloride, gadolinium(III) chloride, iron(II) chloride, iron(III) chloride, niobium(V) chloride, osmium(III) chloride, ruthenium(III) chloride, samarium (III) chloride, tantalum(V) chloride, terbium (III) chloride, and combinations thereof.

4. The nanosphere as recited in claim 1, wherein said ionic salt is selected from the group consisting of sodium metaborates, sodium arsenates, sodium silicates, and combinations thereof.

5. The nanosphere as recited in claim 1, wherein said first anionic surfactant is selected from the group consisting of sodium dodecyl sulfate, sodium dioctyl sulfosuccinate, and combinations thereof.

6. The nanosphere as recited in claim 1, wherein said second anionic surfactant is selected from the group consisting of sodium dodecyl sulfate, sodium dioctyl sulfosuccinate, and combinations thereof.

7. The nanosphere as recited in claim 1, wherein said polymerizable monomer is styrene, methyl methacrylate, and combinations thereof.

8. The nanosphere as recited in claim 1, wherein said polymer shell is formed by adding cross-linking agents to said aqueous solution containing said monomer and said first organic acid.

9. The nanosphere as recited in claim 1 wherein the spacer of said first organic acid includes at least four carbon atoms.

10. The nanosphere as recited in claim 9, wherein the spacer is a phenyl ring.

11. The nanosphere as recited in claim 1, wherein said first organic acid is selected from the group consisting of 4-vinyl benzoic acid, citronellic acid, and combinations thereof.

12. The nanosphere as recited in claim 1, further including a second organic acid, having an acid functionality and a terminal olefin, said second acid being added to said aqueous solution with said first organic acid.

13. The nanosphere as recited in claim 12, wherein said second organic acid is methacrylic acid.

14. The nanosphere as recited in claim 1, further including an ester, having an ester functionality and a terminal olefin, said ester being added to said aqueous solution with said first organic acid.

15. The nanosphere as recited in claim 1, further including an organic alcohol, having an alcohol functionality and a terminal olefin, said alcohol being added to said aqueous solution with said first organic acid.

16. A nanometer-scale bead, having an essentially spherical shape and a diameter of from about 10 nm to about 50 nm, said nanosphere comprising:

a nanometer-scale probe ion core, formed from an ionic salt consisting of any water soluble inorganic anion or cation having a labile counterion;

a molecular layer of a first anionic surfactant, surrounding said probe ion core, wherein said first anionic surfactant is selected from the group consisting of sodium dodecyl sulfate, sodium dioctyl sulfosuccinate, and combinations thereof;

a molecular layer of a second anionic surfactant, surrounding said probe ion core and said first anionic surfactant layer such that the surfactant molecules of said second surfactant are oriented tail-to-tail with the molecules of said first surfactant, wherein said second anionic surfactant is selected from the group consisting of sodium dodecyl sulfate, sodium dioctyl sulfosuccinate, and combinations thereof;

a semi-permeable polymer shell, being formed of polymer chains formed from a polymerizable organic monomer by the addition of an initiator, and encasing said probe ion core within said shell;

a first organic acid having an acid functionality, a terminal olefin and a spacer of at least 5 Å between the acid functionality and the olefin, wherein said first organic acid is selected from the group consisting of 4-vinyl benzoic acid, citronellic acid, and combination thereof, said fist organic acid being incorporated into the polymer chains of said polymer shell;

a second organic acid having an acid functionality and a terminal olefin, being incorporated into the polymer chains of said shell;

an ester, having an ester functionality and a terminal olefin, being incorporated into the polymer chains of said shell; and an organic alcohol, having an alcohol functionality and a terminal olefin, being incorporated into the polymer chains of said shell, the nanosphere being formed by the steps of:
(a) dispersing said first anionic surfactant in a non-polar organic solvent;
(b) dispersing said second anionic surfactant in an aqueous solution;
(c) adding a concentrated aqueous solution of said ionic salt to said surfactant-containing organic solvent, allowing said salt to be dispersed into said first surfactant to form a reverse micelle;
(d) adding said surfactant-containing organic solvent to said surfactant-containing aqueous solution, and allowing the reverse micelle to be dispersed into said second surfactant to form a double micelle;
(e) evaporating said organic solvent away from said aqueous solution containing said double micelles;
(f) adding to said aqueous solution said polymerizable monomer, said first organic acid, said second organic acid, said ester, and said alcohol;
(g) then adding to said aqueous solution said initiator, and activating said initiator, while mixing said aqueous solution, and allowing a polymerization reaction to proceed until the reaction is essentially complete and said double micelles are encapsulated in polymer shells to form nanospheres wherein each nanosphere has a diameter of or about 10 nanometers to about 50 nanometers; and
(h) removing said aqueous solution from the nanospheres.

17. A method of making a nanometer-scale bead, having an essentially spherical shape and a diameter of from about 10 nm to abut 50 nm, comprising the steps of:
making a surfactant-containing organic solvent by dispersing a first anionic surfactant in a non-polar organic solvent;
making a surfactant-containing aqueous solution by dispersing a second anionic surfactant in an aqueous solution;
adding a concentrated aqueous solution of said ionic salt to said surfactant-containing organic solvent, allowing said salt to be dispersed into said first surfactant to form a reverse micelle;
adding said surfactant-containing organic solvent to said surfactant-containing aqueous solution, and allowing the reverse micelle to be dispersed into said second surfactant to form a double micelle wherein the surfactant molecules of said second surfactant are oriented tail-to-tail wit the molecules of said first surfactant;
evaporating said organic solvent away from said aqueous solution containing said double micelles;
adding to said aqueous solution a polymerizable organic monomer, and a first organic acid having an acid functionality, a terminal olefin, and a spacer of at least 5 Å;
then adding to said aqueous solution an initiator, then activating said initiator while mixing said aqueous solution, and allowing a polymerization reaction to proceed until the reaction is essentially complete and said double micelles are encapsulated in polymer shells to form nanospheres wherein each nanosphere has a diameter of from about 10 nanometers to about 50 nanometers; and
removing said aqueous solution from the nanospheres.

18. The method of making a nanosphere as recited in claim 17 further including the step of adding a second organic acid having an acid functionality and a terminal olefin, to said aqueous solution, after evaporating said organic solvent and before adding said initiator.

19. The method of making a nanosphere as recited in claim 17 further including the step of adding an ester, having an ester functionality and a terminal olefin, to said aqueous solution, after evaporating said organic solvent and before adding said initiator.

20. The method of making a nanosphere as recited in claim 17 further including the step of adding an organic alcohol having an alcohol functionality and a terminal olefin, to said aqueous solution, after evaporating said organic solvent and before adding said initiator.

21. The method of making a nanosphere as recited in claim 17 further including the step of adding a base to said organic solvent after adding said particles and before adding said organic solvent to said aqueous solution.

22. The nanosphere as recited in claim 16, wherein said probe ion core is produced by adding a base to said organic solvent after formation of the reverse micelles from said first surfactant and said ionic salt.

23. The nanosphere as recited in claim 16 wherein said ionic salt is selected from the group consisting of dysprosium(III) chloride, europium(III) chloride, gadolinium(III) chloride, iron(II) chloride, iron(III) chloride, niobium(V) chloride, osmium(III) chloride, ruthenium(III) chloride, samarium(III) chloride, tantalum (V) chloride, terbium (III) chloride, and combinations thereof.

24. The nanosphere as recited in claim 16 wherein said ionic salt is selected from the group consisting of sodium metaborates, sodium arsenates, sodium silicates, and combinations thereof.

25. The nanosphere as recited in claim 16 wherein said monomer is styrene, methyl methacrylate, and combinations thereof.

26. The nanosphere as recited in claim 16 wherein said polymer shell is formed by adding cross-linking agents to said aqueous solution containing said monomer and said first organic acid.

27. The nanosphere as recited in claim 16 wherein the spacer of said first organic acid includes at least four carbon atoms.

28. The nanosphere as recited in claim 27, wherein the spacer is a phenyl ring.

29. The nanosphere as recited in claim 16 wherein said second organic acid is methacrylic acid.

* * * * *